(12) United States Patent
Ravetch et al.

(10) Patent No.: US 10,167,332 B2
(45) Date of Patent: *Jan. 1, 2019

(54) POLYPEPTIDES WITH ENHANCED ANTI-INFLAMMATORY AND DECREASED CYTOTOXIC PROPERTIES AND RELATING METHODS

(75) Inventors: Jeffrey V. Ravetch, New York, NY (US); Yoshikatsu Kaneko, Niigata (JP); Nimmerjahn Falk, Erlangen (DE)

(73) Assignee: The Rockefeller University, New York, NY (US)

( * ) Notice: Subject to any disclaimer, the term of this patent is extended or adjusted under 35 U.S.C. 154(b) by 1076 days.

This patent is subject to a terminal disclaimer.

(21) Appl. No.: 12/294,883

(22) PCT Filed: Apr. 3, 2007

(86) PCT No.: PCT/US2007/008396
§ 371 (c)(1),
(2), (4) Date: Jun. 30, 2010

(87) PCT Pub. No.: WO2007/117505
PCT Pub. Date: Oct. 18, 2007

(65) Prior Publication Data
US 2010/0278808 A1    Nov. 4, 2010

Related U.S. Application Data

(60) Provisional application No. 60/789,384, filed on Apr. 5, 2006.

(51) Int. Cl.
| *A61K 39/395* | (2006.01) |
| *C07K 16/00* | (2006.01) |
| *C07K 16/06* | (2006.01) |
| *C07K 16/18* | (2006.01) |
| *C12P 21/00* | (2006.01) |
| *G01N 33/68* | (2006.01) |
| *A61K 47/68* | (2017.01) |
| *A61K 39/00* | (2006.01) |

(52) U.S. Cl.
CPC .............. *C07K 16/00* (2013.01); *A61K 47/68* (2017.08); *C07K 16/06* (2013.01); *C07K 16/18* (2013.01); *C12P 21/005* (2013.01); *G01N 33/6854* (2013.01); *A61K 2039/505* (2013.01); *C07K 2317/41* (2013.01); *C07K 2317/52* (2013.01); *C07K 2317/71* (2013.01); *C07K 2317/76* (2013.01)

(58) Field of Classification Search
None
See application file for complete search history.

(56) References Cited

U.S. PATENT DOCUMENTS

| 4,719,107 A | 1/1988 | Carosella et al. |
| 6,156,881 A | 12/2000 | Seed et al. |
| 6,391,507 B1 | 5/2002 | Macholdt |
| 6,656,466 B1 | 12/2003 | Etcheverry et al. |
| 7,064,191 B2 | 6/2006 | Shinkawa |
| 7,427,469 B2 | 9/2008 | Amara et al. |
| 8,470,318 B2 * | 6/2013 | Ravetch ............... C07K 16/06 424/130.1 |
| 2002/0045207 A1 | 4/2002 | Krummen et al. |
| 2002/0164328 A1 | 11/2002 | Shinkawa et al. |
| 2004/0202658 A1 | 10/2004 | Benyunes |
| 2005/0123546 A1 | 6/2005 | Umana |
| 2005/0181359 A1 | 8/2005 | Optelten et al. |
| 2006/0030521 A1 * | 2/2006 | DeFrees et al. .................. 514/8 |
| 2007/0041979 A1 | 2/2007 | Raju et al. |
| 2007/0048740 A1 | 3/2007 | Isogai et al. |
| 2008/0025913 A1 | 1/2008 | Bowdish et al. |
| 2008/0206246 A1 | 8/2008 | Ravetch et al. |
| 2008/0286819 A1 | 11/2008 | Ravetch et al. |
| 2009/0004179 A1 | 1/2009 | Ravetch |

FOREIGN PATENT DOCUMENTS

| EA | 200870411 | 4/2009 |
| EP | 0666757 A1 | 8/1995 |
| EP | 1020528 | 7/2000 |
| EP | 2010566 | 3/2014 |
| WO | 1996/39488 | 12/1996 |
| WO | 2000/63403 | 10/2000 |
| WO | 200230954 A1 | 4/2002 |
| WO | 02/40047 A2 | 5/2002 |
| WO | 2004/058944 | 7/2004 |
| WO | 2005033135 A1 | 4/2005 |
| WO | 2005/063808 | 7/2005 |
| WO | 2007/005786 | 1/2007 |
| WO | 2007055916 | 5/2007 |
| WO | 2007/117505 | 10/2007 |
| WO | 2008/057634 | 5/2008 |

(Continued)

OTHER PUBLICATIONS

Vitetta et al. Science 2006 313:308-309.*

(Continued)

*Primary Examiner* — Chun W Dahle
(74) *Attorney, Agent, or Firm* — Fish & Richardson P.C.

(57) ABSTRACT

The invention provides a polypeptide containing at least one IgG Fc region region, said polypeptide having a higher anti-inflammatory activity and a lower cytotoxic activity as compared to an unpurified antibody and methods of production of such polypeptide.

4 Claims, 11 Drawing Sheets

(56) References Cited

FOREIGN PATENT DOCUMENTS

| WO | 2009/79382 | 6/2009 |
|---|---|---|
| WO | 2009086262 | 7/2009 |

OTHER PUBLICATIONS

Kaneko et al. Science 2006 vol. 313, pp. 670-673.*
Burton et al. Science 2006 313:627-628.*
Jefferis. Nature Technology 2006 24;10:1230-1231.*
Kaveri et al. The New England Journal of Medicine, 2008 359;3:307-309.*
Gruss et al. Annals of Oncology 1996, 7 (Suppl. 4):S19-S26.*
Jin et al. J. Infect. Dis. 1994, 170;5:1323-1326.*
Bragonzi et al. Biochemica et Biophysica Acta. 2000, 1474:273-282.*
Stadlmann et al., "A close look at human IgG sialylation and subclass distribution after lectin fractionation," Proteomics (2009): vol. 9; pp. 4143-4153.
Stadlmann et al., "Analytical and functional aspects of antibody sialylation," J Clin Immunol (published online: Apr. 14, 2010).
Office Action dated Mar. 18, 2010 for U.S. Appl. No. 12/428,402.
Hodges et al., "Activation of the lectin DC-Sign induces an immature dendritic cell phenotype triggering Rho-GTPase activity required for HIV-1 replication," Nature Immunology (2007); vol. 8: pp. 569-570.
Caparros, et al., "DC-SIGN litigation on dendritic cells results in ERK an dP13k activation and modulates cytokine production," Blood (2006); vol. 107: pp. 3950-3958.
Elomaa et al., "Cloning of a Novel Bacteria-Binding Receptor Structurally Related to Scavenger Receptors and Expressed in a Subset of Macrophages," Cell (1995); vol. 80: pp. 603-609.
Galustian et al.; High and Low Affinity Carbohydrate ligands revealed for murine SIGN-R1 by carbohydrate array and cell binding approaches, and differing specificities for SIGN-R3 and langerin, International Immunology, May 2004, p. 853-867, vol. 16, The Japanese Society for Immunology, Japan.
Tailleux et al.; DC-SIGN is the Major *Mycobacterium tuberculosis* Receptor on Human Dendritic Cells, Journal of Experimental Medicine, Jan. 2003, p. 121-127, vol. 197, The Rockefeller University Press, USA.
Pohlmann et al., Hepatitis C Virus Glycoproteins Interact with DC-SIGN and DC-SIGNR, Journal of Virology, Apr. 2003, p. 4070-4080, vol. 77, American Society for Microbiology, USA.
Geijtenbeck et al., Identification of DC-SIGN, a Novel Dendritic Cell-Specific ICAM-3 Receptor that Supports Primary Immune Responses, Cell, Mar. 2000, p. 575-585, vol. 100, Cell Press, USA.
Takai et al., The Study of Allergy by Japanese Researchers: a historical perspective, International Immunology, 1996, p. 1311-1316, vol. 21, No. 12, The Japanese Society for Immunology, Japan.
Lanoue et al., SIGN-R1 Contributes to Protection against Lethal Pneumococcal Infection in Mice, Journal of Experimental Medicine, Dec. 2004, p. 1383-1393, vol. 200, No. 11, The Rockefeller University Press, USA.
Kang et al., A Dominant Complement Fixation Pathway for Pneumococcal Polysaccharides Initiated by SIGN-R1 Interacting with C1q, Cell, Apr. 2006, p. 47-58, vol. 125, Cell Press, USA.
Van Der Laan et al., Regulation and Functional Involvment of Macrophage Scavenger Receptor MARCO in Clearance of Bacteria in Vivo, The Journal of Immunology, Jan. 1999, p. 939-947, vol. 162, No. 2, The American Association of Immunologists, Inc., USA.
Requena et al., Inhibition of HIV-1 Transmission in trans from dendritic cells to CD4+ T lymphocytes by natural antibodies to the CRD domain of DC-SIGN purified from breast milk and intravenous immunoglobulins, Immunology, Apr. 2008, p. 508-518, vol. 123, No. 4, Blackwell Publishing, USA.
Anthony et al., "Recapitulation of IVIG anti-inflammatory activity with a recombinant IgG Fc", Science, Apr. 2008, p. 373-376, vol. 320, No. 5874, American Association for the Advancement of Science, High Wire Press, USA.
Boruchov, A.M. et al., "Activating and Inhibitory IgG Fc Receptors on Human DCs Mediate Opposing Functions", The Journal of Clinical Investigation, Oct. 2005, p. 2914-2923, vol. 115, No. 10., JCI, USA.
International Search Report, International Application No. PCT/US06/41791 (WO2007/055916), dated Aug. 2007, World Intellectual Property Organization, Geneva.
Office Action dated Jan. 20, 2010 for U.S. Appl. No. 12/013,212.
Buchacher et al., "Purification of intravenous immunoglobulin G from human plasma—aspects of yield and virus safety," Biotechnology Journal (2006); vol. 1, pp. 148-163.
Kemminer et al., "Production of Molecular Characterization of Clinical Phase I Anti-melanoma Mouse IgG3 Monoclonal Antibody R24," Biotechnol. Prog. (2001); vol. 17, pp. 809-821.
Varki, "Loss of N-glycolylneuraminic acid in humans: Mechanisms, consequences, and implications for hominid evolution," Am J Phys Anthropol. (2001); Suppl 33:54-69 (Abstract Only).
Office Action dated Jan. 24, 2011 for U.S. Appl. No. 11/957,015.
Kaneko et al., "Anti-Inflammatory activity of Immunoglobulin G Resulting from FC Slalylation,"; Science (Aug. 1, 2006); vol. 313, No. 5787; pp. 670-673.
Jassal et al., "Sialylation of human IgG-Fc carbohydrate by transfected rat alpha2,6-sialyltransferase,"; Biochemical and Biophysical Research Communications (2001); vol. 286, pp. 243-249.
Scallon et al., "Higher levels of sialylated Fc glycans in immunoglobulin G molecules can adversely impact functionality,"; Molecular immunology (2007); vol. 44, No. 7; pp. 1524-1534.
Raju et al., "Glycoengineering of therapeutic glycoproteins: In vitro galactosylation and sialylation of glycoproteins with terminal N-acetylglucosamine and galactose residues,"; Biochemistry (2001); vol. 40, pp. 8868-8876.
Dalziel et al., "Lectin analysis of 24 human immunoglobulin G N-glycan sialylation," Glycoconjugate Journal (1999); vol. 16, pp. 801-807.
Wang et al., "The immobilized leukoagglutinin from the seeds of maackia-amurensis binds with high affinity to complex-type asn-linked oligosaccharides containing terminal sialic acid-linked alpha-2 3 to penultimate galactose residues,"; Journal of Biological Chemistry (1988); vol. 263, No. 10; pp. 4576-4585.
Nimmerjahn et al., "The antiinflammatory activity of IgG: the intravenous IgG paradox,"; Journal of Experimental Medicine (Jan. 2007); vol. 204, No. 1; pp. 11-15.
Extended European Search Report issued for EP Application No. 07812601.8 dated Apr. 14, 2010.
Weikert et al, "Engineering Chinese Hamster Ovary Cells to Maximize Sialic Acid Content of Recombinant Glycoproteins," Nature Biotechnology (Nov. 1999); vol. 17: 1116-1121.
International Search Report and Written Opinion issued for PCT/US07/8396.
International Search Report and Written Opinion issued for PCT/US08/86622.
International Search Report and Written Opinion issued for PCT/US08/72771.
Extended European Search Report issued for EP Application No. 07754846.9 dated Apr. 9, 2010.
Higuchi et al., "Characterization of the rabbit homolog of human MUC1 glycoprotein isolated from bladder by affinity chromatography on immoblized jacalin," Gycobiology (Jan. 1, 2000): vol. 10, No. 7, pp. 659-667
Qiu et al., "Use of multidimensional lectin affinity chromatography in differential glycoproteomics," Analytical Chemistry (May 1, 2005); vol. 77, No. 9, pp. 2802-2809.
United States Office Action dated Jun. 29, 2010 for U.S. Appl. No. 11/957,015.
United States Office Action dated Mar. 24, 2010 for U.S. Appl. No. 11/957,015.
International Search Report and Written Opinion for PCT/US07/08396.
International Search Report and Written Opinion for PCT/US08/86622.
Arnold et al., "The impact of glycosylation on the biological function and structure of human immunoglobulins," Annu. Rev. Immunol. (2007) vol. 25, pp. 21-50.

(56) References Cited

OTHER PUBLICATIONS

Brekke et al., "Therapeutic antibodies for human diseases at the dawn of the twenty-first century," Nature Reviews Drug Dsicover (Jan. 2003): vol. 2: pp. 52-62.
Gary S. Firestein, "Evolving concepts of rheumatoid arthritis," Nature (May 2003); vol. 425:356-361.
Third Party Observation for application No. EP20070754846, dated May 19, 2014, pp. 1-4.
J. Axford et al., "Presentation: Sialylation Differences between Different Commercial Preparations of Intravenous Immune Globulin (IVIG): Implications for Efficacy," American College of Rheumatology, p. 1639 (2007).
Extended European Search Report from corresponding Application No. 14183260.0, dated Dec. 16, 2014, pp. 1-12.
Kasermann et al., "Analysis and Functional Consequences of Increased Fab-Sialylation of Intravenous Immunoglobulin (IVIG) after Lectin Fractionation," PLOS One, 7(6):1-11—Jun. 2012.
Kumpel et al., "Galactosylation of human IgG monoclonal anti-D produced by EBV-transformed B-lymphoblastoid cell lines is dependent on culture method and affects Fc receptor-mediated functional activity," Hum. Antibod. Hybridomas, 5:143-151 (1994).
Guhr et al., "Enrichment of Sialylated IgG by Lectin Fractionation Does Not Enhance the Efficacy of Immunoglobulin G in a Murine Model of Immune Thrombocytopenia," PLOS One, 6(6):1-8, Jun. 2011.
Leontyev et al., "Sialylation-independent mechanism involved in the amelioration of murine immune thrombocytopenia using intravenous gammaglobulin," Transfusion, 52:1799-1805 Aug. 2012.
PCT Request of corresponding Application No. PCT/US2007/008396, dated Mar. 4, 2007, pp. 1-5.
Morel et al., "Functional CD32 molecules on human NK cells—Abstract," Leuk Lymphoma, Sep. 1999;35(1-2); 47-56.
Tai et al., "A sub-population of keratan sulphates derived from bovine articular cartilage is capped with $\alpha(2$-$6)$-linked N-acetylneuraminic acid residues," Biochem. J. (1992) 286, 231-234.
Nandini Shetty, "Cell-Mediated Immunity," Immunology, p. 123 (1994).
Scallon et al., "Higher levels of sialylated Fc glycans in immunoglobulin G molecules can adversely impact functionality," Molecular Immunology 44(2007) 1524-1534.
U.S. Appl. No. 60/789,384, filed Apr. 5, 2006, Ravetch et al.

Schiff et al., "Rapid infusion of Sandoglobulin in patients with primary humoral immunodeficiency," J. Allergy Clin. Immunol., vol. 88(1): pp. 61-67 (1991).
Notice of Opposition in corresponding EP Application No. 07754846.9, dated Jun. 3, 2015, pp. 1-33.
Raymond et al. "Production of Highly Sialylated Monoclonal Antibodies," INTECH, 2012, Chapter 17, pp. 397-418.
Ravetch et al., "IgG Fc Receptors," Annu. Rev. Immunol. 2001 19:275-90.
Schwarz et al, "Site-specific labelling of the oligosaccharide chains of antibodies," FEBS Letters, 337:213-216, 1994.
Samuelsson et al., "Anti-inflammatory activity of IVIG mediated through the inhibitory Fc receptor," Science, 291:484-486, 2001.
Raju et al., "Species-specific variation in glycosylation of IgG: evidence for the species-specific sialylation and branch-specific galactosylation and importance for engineering recombinant glycoprotein therapeutics," Glycobiology, 10(5):477-486, 2000.
Brecht et al., "Continuous GMP Production in Hollow Fibre Bioreactors—A Viable Alternative for The Production of Low Volume Biopharmaceuticals," Animal Cell Technology meets Genomics, 743-745, 2005.
Boyd et al., "The effect of the removal of sialic acid, galactose and total carbohydrate on the functional activity of Campath-1H," Mol. Immunol., 32(17/18):1311-1318, 1996.
Lemieux et al., "Therapeutic intravenous immunoglobulins," Molecular Immunology 42 (2005) 839-848.
Rini JM. "Lectin Structure" Annu Rev Biophys Biomol Struct., 1995, vol. 24, p. 551-577.
Anthony et al., "Identification of a receptor required for the anti-inflammatory activity of IVIG", PNAS, Dec. 16, 2008, vol. 105, No. 50; 19571-19578.
Schwab et al., "IVIg-mediated amelioration of ITP in mice is dependent on sialic acid and SIGNR1", Eur. J. Immunol. 2012, 42, 826-830.
Schwab et al., "Broad requirement for terminal sialic acid residues and FcγRIIB for the preventive and therapeutic activity of intravenous immunoglobulins in vivo", Eur. J. Immunol., 2014, 44, 1444-1453.
Response to Notice of Opposition in EP Application No. EP07754846.9, dated Jan. 18, 2016, pp. 1-14.
Preliminary Opinion of Opposition Division in EP Application No. EP07754846.9, dated May 2, 2016, pp. 1-4.

* cited by examiner

| Mass (m/z) (humam/mouse) | Composition |
|---|---|
| 1835/1835 | GlcNAc$_2$Man$_3$GlcNAc$_2$Fuc |
| 1865/1865 | GalGlcNAc$_2$Man$_3$GlcNAc$_2$ |
| 2040/2040 | GalGlcNAc$_2$Man$_3$GlcNAc$_2$Fuc |
| 2070/2070 | Gal$_2$GlcNAc$_2$Man$_3$GlcNAc$_2$ |
| 2244/2244 | Gal$_2$GlcNAc$_2$Man$_3$GlcNAc$_2$Fuc |
| 2401 | Neu5AcGalGlcNAc$_2$Man$_3$GlcNAc$_2$Fuc |
| 2432 | Neu5GcGal$_2$GlcNAc$_2$Man$_3$GlcNAc$_2$Fuc |
| 2490/2490 | Gal$_2$GlcNAc$_2$Man$_3$(GlcNAc)GlcNAc$_2$Fuc |
| 2606 | Neu5AcGal$_2$GlcNAc$_2$Man$_3$GlcNAc$_2$Fuc |
| 2637 | Neu5GcGal$_2$GlcNAc$_2$Man$_3$GlcNAc$_2$Fuc |
| 2851 | Neu5AcGal$_2$GlcNAc$_2$Man$_3$(GlcNAc)GlcNAc$_2$Fuc |
| 2882 | Neu5GcGal$_2$GlcNAc$_2$Man$_3$(GlcNAc)GlcNAc$_2$Fuc |
| 2965 | Neu5Ac$_2$Gal$_2$GlcNAc$_2$Man$_3$GlcNAc$_2$Fuc |
| 3028 | Neu5Gc$_2$Gal$_2$GlcNAc$_2$Man$_3$GlcNAc$_2$Fuc |
| 3212 | Neu5Ac$_2$Gal$_2$GlcNAc$_2$Man$_3$(GlcNAc)GlcNAc$_2$Fuc |
| 3275 | Neu5Gc$_2$Gal$_2$GlcNAc$_2$Man$_3$(GlcNAc)GlcNAc$_2$Fuc |

FIG. 5

POLYPEPTIDES WITH ENHANCED ANTI-INFLAMMATORY AND DECREASED CYTOTOXIC PROPERTIES AND RELATING METHODS

CROSS REFERENCE TO RELATED APPLICATIONS

This application is a National Stage of a PCT Application PCT/US07/08396 filed on Apr. 3, 2007, which claims priority to U.S. Provisional Patent Application Ser. No. 60/789,384 filed on Apr. 5, 2006.

STATEMENT REGARDING FEDERALLY FUNDED RESEARCH

The Research leading to the present invention was supported in part, by National Institutes of Health Grant No. AI034662. Accordingly, the U.S. Government has certain rights in this invention.

FIELD OF THE INVENTION

The present invention relates to novel methods for designing therapeutic polypeptides for treatment of inflammatory diseases.

BACKGROUND OF THE INVENTION

Although cellular receptors for immunoglobulins were first identified nearly 40 years ago, their central role in the immune response was only discovered in the last decade. They are key players in both the afferent and efferent phase of an immune response, setting thresholds for B cell activation and antibody production, regulating the maturation of dendritic cells and coupling the exquisite specificity of the antibody response to effector pathways, such as phagocytosis, antibody dependent cellular cytotoxicity and the recruitment and activation of inflammatory cells. Their central role in linking the humoral immune system to innate effector cells has made them attractive immunotherapeutic targets for either enhancing or restricting the activity of antibodies in vivo.

The interaction of antibodies and antibody-antigen complexes with cells of the immune system effects a variety of responses, including antibody dependent cell-mediated cytotoxicity (ADCC) and complement dependent cytotoxicity (CDC), phagocytosis, inflammatory mediator release, clearance of antigen, and antibody half-life (reviewed in Daron, *Annu Rev Immunol*, 15, 203-234 (1997); Ward and Ghetie, *Therapeutic Immunol*, 2, 77-94 (1995); Ravetch and Kinet, *Annu Rev Immunol*, 9, 457-492 (1991)), each of which is incorporated herein by reference).

Antibody constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, and IgG4; IgA1 and IgA2. The heavy chain constant regions that correspond to the different classes of immunoglobulins are called $\alpha$, $\delta$, $\varepsilon$, $\gamma$, and $\mu$, respectively. Of the various human immunoglobulin classes, human IgG1 and IgG3 mediate ADCC more effectively than IgG2 and IgG4.

Papain digestion of antibodies produces two identical antigen binding fragments, called Fab fragments, each with a single antigen binding site, and a residual "Fc" fragment, whose name reflects its ability to crystallize readily. The Fc region is central to the effector functions of antibodies. The crystal structure of the human IgG Fc region has been determined (Deisenhofer, *Biochemistry*, 20, 2361-2370 (1981), which is incorporated herein by reference). In human IgG molecules, the Fc region is generated by papain cleavage N-terminal to Cys, 226.

IgG has long been appreciated to mediate both pro- and anti-inflammatory activities through interactions mediated by its Fc fragment. Thus, while Fc-FcγR interactions are responsible for the pro-inflammatory properties of immune complexes and cytotoxic antibodies, intravenous gamma globulin (IVIG) and its Fc fragments are anti-inflammatory and are widely used to suppress inflammatory diseases. The precise mechanism of such paradoxical properties is unclear but it has been proposed that glycosylation of IgG is crucial for regulation of cytotoxicity and inflammatory potential of IgG.

IgG contains a single, N-linked glycan at $Asn^{297}$ in the CH2 domain on each of its two heavy chains. The covalently-linked, complex carbohydrate is composed of a core, biantennary penta-polysaccharide containing N-acetylglucosamine (GlcNAc) and mannose (man). Further modification of the core carbohydrate structure is observed in serum antibodies with the presence of fucose, branching GlcNAc, galactose (gal) and terminal sialic acid (sa) moieties variably found. Over 40 different glycoforms have thus been detected to be covalently attached to this single glycosylation site. Fujii et al., *J. Biol. Chem.* 265, 6009 (1990). Glycosylation of IgG has been shown to be essential for binding to all FcγRs by maintaining an open conformation of the two heavy chains. Jefferis and Lund, *Immune.l Lett.* 82, 57 (2002), Sondermann et al., *J. Mol. Biol.* 309, 737 (2001). This absolute requirement of IgG glycosylation for FcγR binding accounts for the inability of deglycosylated IgG antibodies to mediate' in vivo triggered inflammatory responses, such as ADCC, phagocytosis and the release of inflammatory mediators. Nimmerjahn and Ravetch, *Immunity* 24, 19 (2006). Further observations that individual glycoforms of IgG may contribute to modulating inflammatory responses have been suggested by the altered affinities for individual FcγRs reported for IgG antibodies containing or lacking fucose and their consequential affects on cytotoxicity. Shields et al., *J. Biol. Chem.* 277, 26733 (2002), Nimmerjahn and Ravetch, *Science* 310, 1510 (2005). A link between autoimmune states and specific glycosylation patterns of IgG antibodies has been observed in patients with rheumatoid arthritis and several autoimmune vasculities in which decreased galactosylation and sialylation of IgG antibodies have been reported. Parekh et al., *Nature* 316, 452 (1985), Rademacher et al., *Proc. Natl. Acad. Sci. USA* 91, 6123 (1994), Matsumoto et al., 128, 621 (2000), Holland et al., Biochim. Biophys. Acta Dec 27; [Epub ahead of print] 2005. Variations in IgG glycoforms have also been reported to be associated with aging and upon immunization, although the in vivo significance of these alterations have not been determined. Shikata et al., *Glycoconj. J.* 15, 683 (1998), Lastra, et al., *Autoimmunity* 28, 25 (1998).

Accordingly, there is a need for the development of methods for the generation of polypeptides that would account for the disparate observations of IgG properties in vivo.

SUMMARY OF THE INVENTION

The present invention fills the foregoing need by providing such methods and molecules. In one aspect, the invention provides a polypeptide containing at least one IgG Fc region, said polypeptide having a higher anti-inflammatory activity and a lower cytotoxic activity as compared to an unpurified antibody. In different embodiments of the invention, the polypeptide comprises a human IgG1, IgG2, IgG3 or IgG4 Fc region, said polypeptide having a higher sialic acid content as compared to an unpurified antibody.

In another aspect, the instant invention provides a pharmaceutical formulation comprising a polypeptide containing at least one Fc region having a higher anti-inflammatory activity and a lower cytotoxic activity, in combination with a suitable carrier or diluent.

In yet another aspect, the invention provides a method of preparation of a polypeptide containing at least one Fc region, said polypeptide having a higher anti-inflammatory activity and a lower cytotoxic activity than an unpurified antibody, the method comprising: providing an unpurified source of the polypeptide containing at least one Fc region, the unpurified source of the polypeptide containing at least one Fc region comprising a plurality of polypeptides containing at least one IgG Fc region having sialic acid and a plurality of polypeptides containing at least one IgG Fc region lacking sialic acid; and increasing the ratio of the plurality of the polypeptides containing at least one IgG Fc region having sialic acid to the plurality of the polypeptides containing at least one IgG Fc region lacking sialic acid. In different embodiments of the invention, the ratio of the plurality of the polypeptides containing at least one IgG Fc region having sialic acid to the plurality of the polypeptides containing at least one IgG Fc region lacking sialic acid is achieved either through a removal of the polypeptides containing at least one IgG Fc region lacking sialic acid or through a sialylation of the unpurified source the of polypeptides containing at least one IgG Fc region.

BRIEF DESCRIPTION OF THE DRAWINGS

FIG. 5 illustrates the composition of the carbohydrate moieties released from N297 IgG Fc. The core sugar structure linked to the asparagine residue 297 in the antibody heavy chain is composed of N-acetylglucosamine (GlcNAc) and mannose (Man). Individual glycoforms vary with respect to attachment of one or two terminal galactose (Gal) residues, attachment of terminal sialic acid-(N-acetylneuraminic acid or Neu5Ac for human and N-glycolylneuraminic acid or Neu5Gc for mouse) residues, and/or the attachment of bisecting GlcNAc or fucose (Fuc). Numbers indicate the molecular weight of the different sugar compositions as determined by MALDI-TOF MS. The mass for the glycan structures are indicated for human and mouse (underlined).

DETAILED DESCRIPTION OF THE INVENTION

Figure 1:
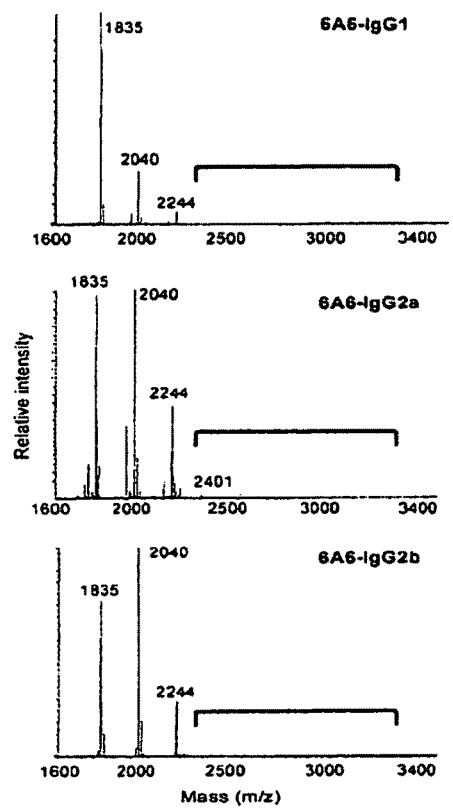
FIG. 1 demonstrates carbohydrate spectra of 6A6-IgG antibody isotypes. N-glycans derived from 6A6-IgG1, IgG2a and IgG2b were analyzed by MALDI-TOF MS. Peaks containing sialic acid residues are indicated by the bracket. Recombinant 6A6 antibody switch variants produced by transient transfection of 293T cells contained minimal levels of sialic acid residues in their Asn-297 attached carbohydrates.

The inventors have surprisingly found that the cytotoxic and anti-inflammatory response of the IgG Fc domain results from the differential sialylation of the Fc-linked core polysaccharide. The cytotoxicity of IgG antibodies is reduced upon sialylation; conversely, the anti-inflammatory activity of IVIG is enhanced. IgG sialylation is shown to be regulated upon the induction of an antigen-specific immune response, thus providing a novel means of switching IgG from an innate, anti-inflammatory molecule in the steady-state, to a adaptive, pro-inflammatory species upon antigenic challenge.

Accordingly, the instant disclosure provides an advantageous strategy of creating and selecting IgGs with desired cytotoxic and anti-inflammatory potential.

Definitions

Throughout the present specification and claims, the numbering of the residues in an immunoglobulin heavy chain is that of the EU index as in Kabat et al., *Sequences of Proteins of Immunological Interest*, 5th Ed. Public Health Service, National Institutes of Health, Bethesda, Md. (1991), which is expressly incorporated herein by reference. The "EU index as in Kabat" refers to the residue numbering of the human IgG1 EU antibody.

The term "native" or "parent" refers to an unmodified polypeptide comprising an Fc amino acid sequence. The parent polypeptide may comprise a native sequence Fc region or an Fc region with pre-existing amino acid sequence modifications (such as additions, deletions and/or substitutions).

The term "polypeptide" refers to any fragment of a protein containing at least one IgG Fc region, including, without limitation, fully functional proteins, such as, for example, antibodies, e.g., IgG antibodies.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof.

The "CH2 domain" of a human IgG Fc region (also referred to as "Cγ2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain (Burton, *Mol Immunol*, 22, 161-206 (1985), which is incorporated herein by reference).

The "CH3 domain" comprises the stretch of residues C-terminal to a CH2 domain in an Fc region (i.e., from about amino acid residue 341 to about amino acid residue 447 of an IgG).

The term "hinge region" is generally defined as stretching from Glu216 to Pro230 of human IgG1 (Burton (1985). Hinge regions of other IgG isotypes may be aligned with the IgG1 sequence by placing the first and last cysteine residues forming inter-heavy chain S—S bonds in the same positions.

The term "binding domain" refers to the region of a polypeptide that binds to another molecule. In the case of an FcR, the binding domain can comprise a portion of a polypeptide chain thereof (e.g., the α chain thereof) which is responsible for binding an Fc region. One exemplary binding domain is the extracellular domain of an FcR chain.

A "functional Fc region" possesses at least a partial "effector function" of a native sequence Fc region. Exemplary "effector functions" include Clq binding; complement dependent cytotoxicity; Fc receptor binding; antibody-dependent cell-mediated cytotoxicity (ADCC); phagocytosis; down regulation of cell surface receptors (e.g., B cell receptor; BCR), etc. Such effector functions generally require the Fc region to be combined with a binding domain (e.g., an antibody variable domain) and can be assessed using various assays as herein disclosed, for example.

A "native sequence Fc region" comprises an amino acid sequence identical to the amino acid sequence of an Fc region found in nature. A "variant Fc region" as appreciated by one of ordinary skill in the art comprises an amino acid sequence which differs from that of a native sequence Fc region by virtue of at least one "amino acid modification." Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and more preferably at least about 90% homology therewith, more preferably at least about 95% homology therewith, even more preferably, at least about 99% homology therewith.

The term "altered glycosylation" refers to a polypeptide, as defined above, be it native or modified, in which the carbohydrate addition to the heavy chain constant region is manipulated to either increase or decrease specific sugar components. For example, polypeptides, such as, for example, antibodies, prepared in specific cell lines, such as, for example, Lec2 or Lec3, may be deficient in the attachment of sugar moieties such as fucose and sialic acid.

The terms "Fc receptor" or "FcR" are used to describe a receptor that binds to the Fc region of an antibody. In one embodiment of the invention, FcR is a native sequence human FcR. In another embodiment, FcR, including human FcR, binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review in Daron, *Annu Rev Immunol*, 15, 203-234 (1997); FcRs are reviewed in Ravetch and Kinet, *Annu Rev Immunol*, 9, 457-92 (1991); Capel et al., *Immunomethods*, 4, 25-34 (1994); and de Haas et al., *J Lab Clin Med*, 126, 330-41 (1995), Nimmerjahn and Ravetch 2006, Ravetch Fc Receptors in Fundemental Immunology, ed William Paul 5$^{th}$ Ed. each of which is incorporated herein by reference).

"Antibody-dependent cell-mediated cytotoxicity" and "ADCC" refer to an in vitro or in vivo cell-mediated reaction in which cytotoxic cells that express FcRs (e.g., monocytic cells such as natural killer (NK) cells and macrophages) recognize bound antibody on a target cell and subsequently cause lysis of the target cell. In principle, any effector cell with an activating FcγR can be triggered to mediate ADCC. One such cell, the NK cell, expresses FcγRIII only, whereas monocytes, depending on their state of activation, localization, or differentiation, can express FcγRI, FcγRII, and FcγRIII. FcR expression on hematopoietic cells is summarized in Ravetch and Bolland, *Annu Rev Immunol*, (2001), which is incorporated herein by reference.

"Human effector cells" are leukocytes which express one or more FcRs and perform effector functions. Preferably, the cells express at least one type of an activating Fc receptor, such as, for example, FcγRIII and perform ADCC effector function. Examples of human leukocytes which mediate ADCC include peripheral blood mononuclear cells (PBMC), natural killer (NK) cells, monocytes, and neutrophils, with PBMCs and NK cells being preferred. The effector cells may be isolated from a native source thereof, e.g., from blood or PBMCs as described herein.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The phrase "sialic acid content" of an antibody refers both to the total number of sialic acid residues on an Fc region of a heavy chain of an antibody and to the ratio of sialylated antibodies to asialylated antibodies in an unpurified antibody preparation, unless the phrase is in a context clearly suggesting that another meaning is intended.

"Antibody fragments", as defined for the purpose of the present invention, comprise a portion of an intact antibody, generally including the antigen binding or variable region of the intact antibody or the Fc region of an antibody which retains FcR binding capability. Examples of antibody fragments include linear antibodies; single-chain antibody molecules; and multispecific antibodies formed from antibody fragments. The antibody fragments preferably retain at least part of the hinge and optionally the CH1 region of an IgG heavy chain. More preferably, the antibody fragments retain the entire constant region of an IgG heavy chain, and include an IgG light chain.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature, 256, 495-497 (1975), which is incorporated herein by reference, or may be made by recombinant DNA methods (see, e.g., U.S. Pat. No. 4,816,567, which is incorporated herein by reference). The monoclonal antibodies may also be isolated from phage antibody libraries using the techniques described in Clackson et al., *Nature*, 352, 624-628 (1991) and Marks et al., *J Mol Biol*, 222, 581-597 (1991), for example, each of which is incorporated herein by reference.

In other embodiments of the invention, the polypeptide containing at least one IgG Fc region may be fused with other protein fragments, including, without limitation, whole proteins. A person of ordinary skill in the art will undoubtedly appreciate that many proteins may be fused with the polypeptide of the present invention, including, without limitation, other immunoglobulins, especially, immunoglobulins lacking their respective Fc regions. Alternatively, other biologically active proteins or fragments thereof may be fused with the polypeptide of the present invention, as described, for example, in the U.S. Pat. No. 6,660,843, which is incorporated herein by reference. This embodiment is especially advantageous for delivery of such biologically active proteins or fragments thereof to cells expressing Fc receptors. Further, different markers, such as, for example, GST tag or green fluorescent protein, or GFP, may be used.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; Morrison et al., *Proc Natl Acad Sci USA*, 81, 6851-6855 (1984); Neuberger et al., *Nature*, 312, 604-608 (1984); Takeda et al., *Nature*, 314, 452-454 (1985); International Patent Application No. PCT/GB85/00392, each of which is incorporated herein by reference).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody optionally also will comprise at least a portion of an immunoglobulin constant region (Fc), typically that of a human immunoglobulin. For further details, see Jones et al., *Nature*, 321, 522-525 (1986); Riechmann et al., *Nature*, 332, 323-329 (1988); Presta, *Curr Op Struct Biol*, 2, 593-596 (1992); U.S. Pat. No. 5,225,539, each of which is incorporated herein by reference.

The polypeptides containing at least one IgG Fc region include those in which specific amino acid substitutions, additions or deletions are introduced into a parental sequence through the use of recombinant DNA techniques to modify the genes encoding the heavy chain constant region. The introduction of these modifications follows well-established techniques of molecular biology, as described in manuals such as Molecular Cloning (Sambrook and Russel, (2001)). In addition, the polypeptides with at least one Fc region will include those polypeptides which have been selected to contain specific carbohydrate modifications, obtained either by expression in cell lines known for their glycosylation specificity (Stanley P., et al., *Glycobiology*, 6, 695-9 (1996); Weikert S., et al., *Nature Biotechnology*, 17, 1116-1121 (1999); Andresen D C and Krummen L., *Current Opinion in Biotechnology*, 13, 117-123 (2002)) or by enrichment or depletion on specific lectins or by enzymatic treatment (Hirabayashi et al., *J Chromatogr B Analyt Technol Biomed Life Sci*, 771, 67-87 (2002); Robertson and Kennedy, *Bioseparation*, 6, 1-15 (1996)). It is known in the art that quality and extent of antibody glycosylation will differ depending on the cell type and culture condition employed. (For example, Patel et al., *Biochem J*, 285, 839-845 (1992)) have reported that the content of sialic acid in antibody linked sugar side chains differs significantly if antibodies were produced as ascites or in serum-free or serum containing culture media. Moreover, Kunkel et al., Biotechnol Prog, 16, 462-470 (2000) have shown that the use of different bioreactors for cell growth and the amount of dissolved oxygen in the medium influenced the amount of galactose and sialic acid in antibody linked sugar moieties. These studies, however, did not address how varying levels of sialic acid residues influence antibody activity in vivo.

Host Expression Systems

The polypeptide of the present invention can be expressed in a host expression system, i.e., host cells, capable of N-linked glycosylation. Typically, such host expression systems may comprise fungal, plant, vertebrate or invertebrate expression systems. In one embodiment the host cell is a mammalian cell, such as a Chinese hamster ovary (CHO) cell line, (e.g. CHO-K1; ATCC CCL-61), Green Monkey cell line (COS) (e.g. COS1 (ATCC CRL-1650), COS 7 (ATCC CRL-1651)); mouse cell (e.g. NS/0), Baby Hamster Kidney (BHK) cell line (e.g. ATCC CRL-1632 or ATCC CCL-10), or human cell (e.g. HEK 293 (ATCC CRL-1573)), or any other suitable cell line, e.g., available from public depositories such as the American Type Culture Collection, Rockville, Md. Further, an insect cell line, such as a Lepidoptora cell line, e.g. Sf9, a plant cell line, a fungal cell line, e.g., yeast such as, for example, *Saccharomyces cerevisiae*, *Pichia pastoris*, *Hansenula* spp. It will be appreciated by one of ordinary skill in the art that in some cases modifications to host cells may be required to insure that N-linked glycosylation and glycan maturation occur to result in a complex, biantennary sugar as typically found on the Fc domain of human IgG (see for example Hamilton, S R, et al. Science, 313, 1441 (2006); Li, H, et al., Nature Biotechnology 24, 210 (2006); Wildt, S and Grengross, T U Nature Reviews Microbiology 3, 119 (2005).

Therapeutic Formulations

Therapeutic formulations comprising the polypeptides containing at least one IgG Fc region can be prepared for storage by mixing the polypeptides of the present invention having the desired degree of purity with optional physiologically acceptable carriers, excipients or stabilizers (see, e.g., Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenyl, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants, such as TWEEN™, PLURONICS™ or polyethylene glycol (PEG).

The formulations herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In preferred embodiments, the formulations to be used for in vivo administration are sterile. The formulations of the instant invention can be easily sterilized, for example, by filtration through sterile filtration membranes.

Sustained-release preparations may also be prepared. Suitable examples of sustained-release preparations include semipermeable matrices of solid hydrophobic polymers containing the modified antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (see, e.g., U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Creation of Sialylated Polypeptides Containing at Least One IgG Fc Region.

The polypeptides of the present invention can be further purified or modified so that they have an increased amount of sialic acid compared to unmodified and/or unpurified antibodies. Multiple methods exist to reach this objective. In one method, the source of unpurified polypeptides, such as, for example, plasma fractions that contain IgG from which IVIG is routinely purified, is passed through the column having lectin, which is known to bind sialic acid. In one embodiment, the lectin is isolated from *Sambuccus nigra*. Thus, a sialylated fraction of the polypeptides containing at least one IgG Fc region will be retained in the column while an asialylated fraction will pass through. The sialylated fraction of the polypeptides containing at least one IgG Fc region can be eluted by another wash with a different stringency conditions. Thus, it is possible to obtain a preparation of the polypeptide of the present invention wherein the content of sialic acid is increased compared to the normal content. Further, one may employ an enzymatic reaction with a sialyltransferase and a donor of sialic acid as described, for example, in the U.S. Pat. No. 20060030521.

Suitable non-limiting examples of sialyltransferase enzymes useful in the claimed methods are ST3Gal III, which is also referred to as $\alpha$-(2,3)sialyltransferase (EC 2.4.99.6), and $\alpha$-(2,6)sialyltransferase (EC 2.4.99.1). Alpha-(2,3)sialyltransferase catalyzes the transfer of sialic acid to the Gal of a Gal-$\beta$-1,3GlcNAc or Gal-$\beta$-1,4GlcNAc glycoside (see, e.g., Wen et al., J. Biol. Chem. 267: 21011 (1992); Van den Eijnden et al., J. Biol. Chem. 256: 3159 (1991)) and is responsible for sialylation of asparagine-linked oligosaccharides in glycopeptides. The sialic acid is linked to a Gal with the formation of an $\alpha$-linkage between the two saccharides. Bonding (linkage) between the saccharides is between the 2-position of NeuAc and the 3-position of Gal. This particular enzyme can be isolated from rat liver (Weinstein et al., J. Biol. Chem. 257: 13845 (1982)); the human cDNA (Sasaki et al. (1993) J. Biol. Chem. 268: 22782-22787; Kitagawa & Paulson (1994) J. Biol. Chem. 269: 1394-1401) and genomic (Kitagawa et al. (1996) J. Biol. Chem. 271: 931-938) DNA sequences are known, facilitating production of this enzyme by recombinant expression.

Activity of $\alpha$-(2,6)sialyltransferase results in 6-sialylated oligosaccharides, including 6-sialylated galactose. The name "$\alpha$-(2,6)sialyltransferase" refers to the family of sialyltransferases attaching sialic acid to the sixth atom of the acceptor polysaccharide. Different forms of a-(2,6)sialyltransferase can be isolated from different tissues. For example, one specific form of this enzyme, ST6Gal II, can be isolated from brain and fetal tissues. Krzewinski-Recchi et al., *Eur. J. Biochem.* 270, 950 (2003).

In addition, a person of average skill in the art will appreciate that cell culture conditions can be manipulated to change the sialylation rate. For example, to increase the sialic acid content, production rate is decreased and osmolality is generally maintained within a lower margin suitable for the particular host cell being cultured. Osmolality in the range from about 250 mOsm to about 450 mOsm is appropriate for increased sialic acid content. This and other suitable cell culture conditions are described in, e.g., U.S. Pat. No. 6,656,466. Patel et al., *Biochem J,* 285, 839-845 (1992) have reported that the content of sialic acid in antibody linked sugar side chains differs significantly if antibodies were produced as ascites or in serum-free or serum containing culture media. Moreover, Kunkel et al., *Biotechnol. Prog.,* 16, 462-470 (2000) have shown that the use of different bioreactors for cell growth and the amount of dissolved oxygen in the medium influenced the amount of galactose and sialic acid in antibody linked sugar moieties.

In another embodiment, host cells, such as, for example, immortalized human embryonic retina cells, may be modified by introducing a nucleic acid encoding a sialyltransferase such as, for example, an α-2,3-sialyltransferase or an α-2,6-sialyltransferase, operably linked to a promoter, such as, for example, a CMV promoter. The α-2,3-sialyltransferase may be the human α-2,3-sialyltransferase, known as SIAT4C or STZ (GenBank accession number L23767), and described, for example, in the U.S. Pat. No. 20050181359.

The nucleic acid encoding the sialyltransferase may be introduced into the host cell by any method known to a person of ordinary skill in the art. Suitable methods of introducing exogenous nucleic acid sequences are also described in Sambrook and Russel, *Molecular Cloning: A Laboratory Manual* (3$^{rd}$ Edition), Cold Spring Harbor Press, NY, 2000. These methods include, without limitation, physical transfer techniques, such as, for example, microinjection or electroporation; transfections, such as, for example, calcium phosphate transfections; membrane fusion transfer, using, for example, liposomes; and viral transfer, such as, for example, the transfer using DNA or retroviral vectors.

The polypeptide containing at least one IgG Fc region may be recovered from the culture supernatant and can be subjected to one or more purification steps, such as, for example, ion-exchange or affinity chromatography, if desired. Suitable methods of purification will be apparent to a person of ordinary skill in the art.

A person of ordinary skill in the art will appreciate that different combinations of sialylation methods, disclosed above, can lead to production of the polypeptides containing at least one IgG Fc region with an extremely high level of sialylation. For example, one can express the polypeptide containing at least one IgG Fc region in the host cells overexpressing sialyltransferase, as described above, and then further enrich the sialylated fraction of these polypeptides by, for example, sialylating these polypeptides in an enzymatic reaction followed by an affinity chromatography using lectin-containing columns. Similarly, an enzymatic reaction followed by affinity chromatography may be used for IVIG source of the polypeptides containing at least one IgG Fc region.

To examine the extent of glycosylation on the polypeptides containing at least one IgG Fc region, these polypeptides can be purified and analyzed in SDS-PAGE under reducing conditions. The glycosylzation can be determined by reacting the isolated polypeptides with specific lectins, or, alternatively as would be appreciated by one of ordinary skill in the art, one can use HPLC followed by mass spectrometry to identify the glycoforms. (Wormald, M R et al., Biochem 36:1370 (1997).

To describe the instant invention in more details, several non-limiting illustrative examples are given below.

EXAMPLES

Example 1

IVIG with Increased Sialic Acid Content Exhibits Decreased Cytotoxicity

To determine if specific glycoforms of IgG are involved in modulating the effector functions of antibodies the role of specific, Asn$^{297}$—linked carbohydrates in mediating the cytotoxicity of defined IgG monoclonal antibodies was explored. The anti-platelet antibodies, derived from the 6A6 hybridoma, expressed as either an IgG1, 2a or 2b switch variant in 293 cells as previously described in Nimmerjahn et al., Immunity 23, 41 (2005) were analyzed by mass spectroscopy to determine their specific carbohydrate composition and structure (FIG. 1). These antibodies contain minimal sialic acid residues. Enrichment of the sialic acid containing species by *Sambucus nigra* lectin affinity chromatography yielded antibodies enriched 60-80 fold in sialic acid content FIG. 2B and FIG. 3). Comparison of the ability of sialylated and asialylated 6A6-IgG1 and 2b antibodies to mediate platelet clearance revealed an inverse correlation between sialylation and in vivo activity. Sialylation of 6A6 IgG antibodies resulted in a 40-80% reduction in biological activity (FIG. 2C and FIG. 3).

To determine the mechanism of this reduction in activity surface plasmon resonance binding was performed on these antibodies for each of the mouse FcYRs and to its cognate antigen.

Surface plasmon resonance analysis was performed as described in Nimmerjahn and Ravetch, Science 310, 1510 (2005). Briefly, 6A6 antibody variants containing high or low levels of sialic acid residues in their sugar side chains were immobilized on the surface of CM5 sensor chips. Soluble Fcy-receptors were injected at different concentrations through flow cells at room temperature in HBS-EP running buffer (10 mM Hepes, pH 7.4, 150 mM NaCl, 3.4 mM EDTA, and 0.005% surfactant P20) at a flow rate of 30 ul/min. Soluble Fc-receptors were injected for 3 minutes and dissociation of bound molecules was observed for 7 minutes. Background binding to control flow cells was subtracted automatically. Control experiments were performed to exclude mass transport limitations. Affinity constants were derived from sensorgram data using simultaneous fitting to the association and dissociation phases and global fitting to all curves in the set. A 1:1 Langmuir binding model closely fitted the observed sensorgram data and was used in all experiments.

Figure 2:
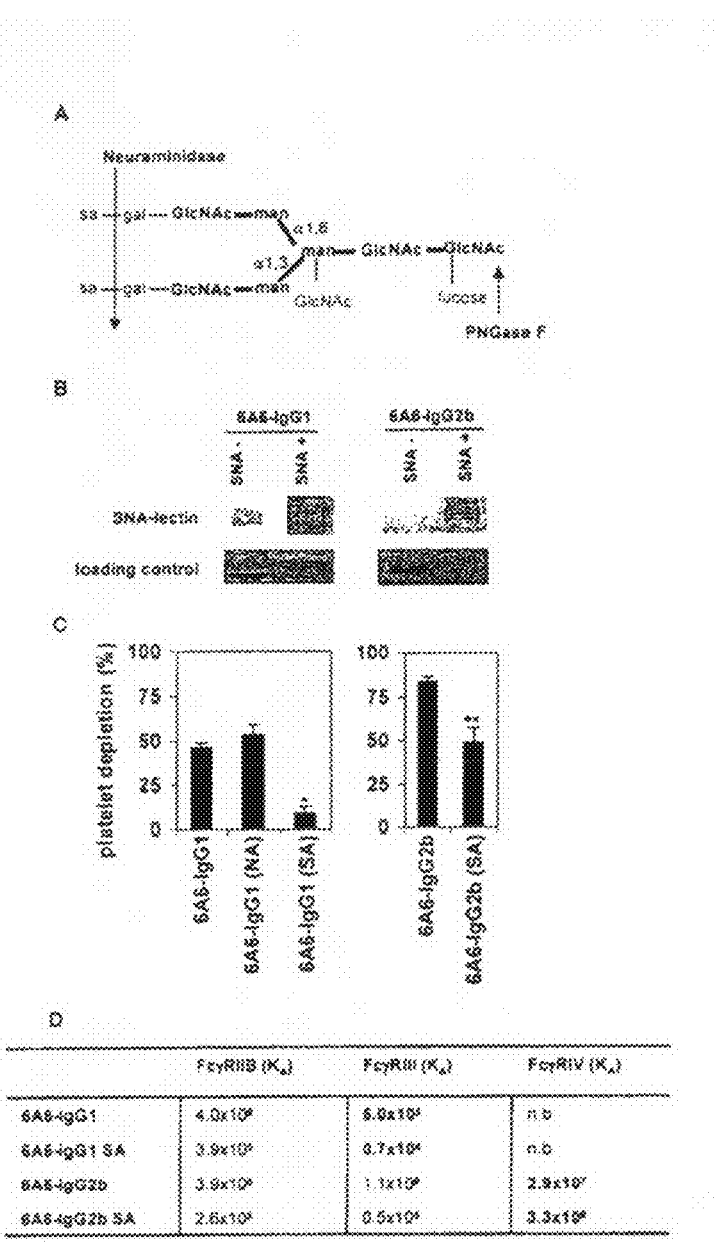
FIG. 2 shows that sialylation reduces IgG cytotoxicity. (A) Structure of the fully processed carbohydrate moiety attached to asparagine 297 (N297) in the antibody Fc-fragment. The core sugar structure is shown in bold. Variable residues such as the terminal and bisecting sugars are underlined and specific linkages are indicated. Cleavage sites for PNGase and neuraminidase are also indicated. This fully processed structure is present in about 5% of the total serum IgG pool (1). Abbreviations: GlcNAc=N-acetyl glucosamine, man=mannose, gal=galactose, sa=sialic acid. (B) Enrichment of 6A6-IgG1 and IgG2b antibodies with high sialic acid content via *Sambucus nigra* agglutinin (SNA) affinity chromatography. (C) In vivo activity of 6A6-IgG1 and -IgG2b antibodies enriched for sialic acid (SA) or depleted for sialic acid by neuraminidase (NA) treatment. 4 µg of each antibody was injected into groups of mice (N=4, mean+/−SEM); * indicates p<0.0001, ** indicates p<0.01. (D) Association constants ($K_A$) for FcγRIIB, FcγRIII and FcγRIV in binding to antibodies with high or low levels of sialylation; n.b. indicates no binding. Bold numbers indicate the isotype specific Fc-receptors that are responsible for mediating antibody activity in vivo. The standard error in all these measurements was below 5%.
Figure 3:
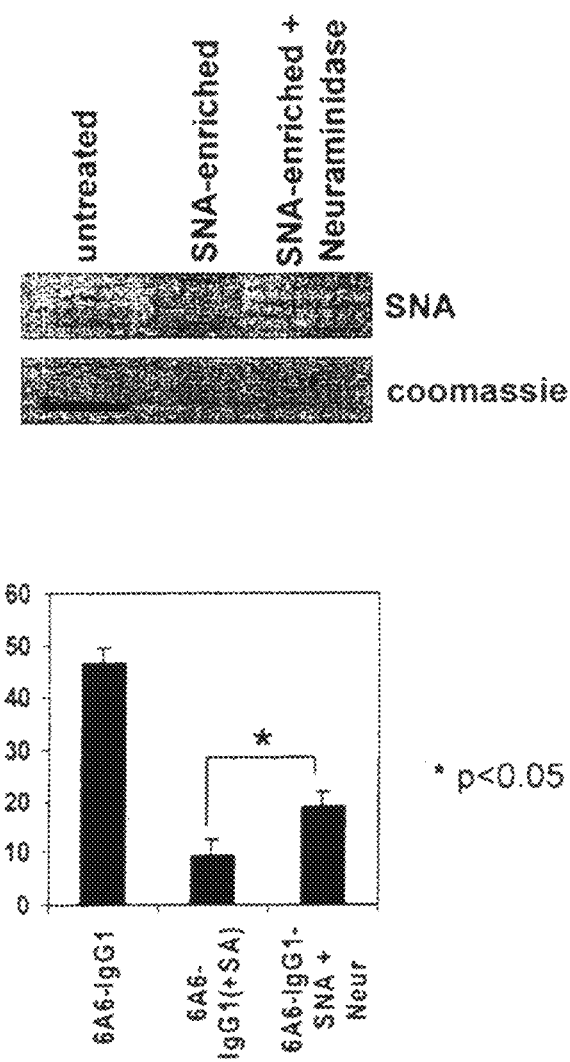
FIG. 3 illustrates that antibody activity in vivo is modulated by sialic acid. 6A6-IgG1 was enriched for sialic acid by affinity chromatography with SNA-agarose. A fraction of this SNA-enriched preparation was treated with neuraminidase (SNA-enriched+Neuraminidase). (A) Sialic acid content in antibody preparations was determined by lectin blotting with SNA. (B) In vivo antibody activity was tested by monitoring platelet depletion induced by injection of 4 µg of the respective antibody preparations (n=4-5 mice per group).

A 5-10 fold reduction in binding affinity was observed for the sialylated forms of these antibodies to their respective activating FcyRs as compared to their asialylated counterparts, while no differences in binding affinity for the antigen were observed (FIG. 2D). Thus, sialylation of the Asn$^{297}$ linked glycan structure of IgG resulted in reduced binding affinities to the subclass-restricted activation FcyRs and thus reduced their in vivo cytotoxicity.

To determine the generality of the observation that sialylation of the N-linked glycan of IgG was involved in modulating its in vivo inflammatory activity, we next examined the role of N-linked glycans on the anti-inflammatory activity of IVIG. This purified IgG fraction obtained from the pooled serum of 5-10,000 donors, when administered intravenously at high doses (1-2 g/kg), is a widely used therapeutic for the treatment of inflammatory diseases. Dwyer, N. Engl. J. Med. 326, 107 (1992). This anti-inflammatory activity is a property of the Fc fragment and is protective in murine models of ITP, RA and nephrotoxic nephritis. Imbach et al., Lancet 1, 1228 (1981), Samuelsson et al., Science 291, 484 (2001), Bruhns et al., Immunity 18, 573 (2003), Kaneko et al., J. Exp. Med. 203, 789 (2006)

A common mechanism for this anti-inflammatory activity was proposed involving the induction of surface expression of the inhibitory FcyRIIB molecule on effector macrophages, thereby raising the threshold required for cytotoxic IgG antibodies or immune complexes to induce effector cell responses by activation FcγR triggering. Nimmerjahn and Ravetch, *Immunity* 24, 19 (2006).

Example 2

De-Sialylation of IVIG Decreases the Anti-Inflammatory Effect of IVIG in Mouse Arthritis Model Mice C57BL/6 and NOD mice were purchased from the Jackson Laboratory (Bar Harbor, Me.). FcγRIIIB$^{-/-}$ mice were generated in the inventors' laboratory and backcrossed for 12 generations to the C57BL/6 background. KRN TCR transgenic mice on a C57BL/6 background (K/B) were gifts from D. Mathis and C. Benoist (Harvard Medical School, Boston, Mass.) and were bred to NOD mice to generate K/B×N mice. Female mice at 8-10 weeks of age were used for all experiments and maintained at the Rockefeller University animal facility. All experiments were done in compliance with federal laws and institutional guidelines and have been approved by the Rockefeller University (New York, N.Y.).

Antibodies and Soluble Fc Receptors

6A6 antibody switch variants were produced by transient transfection of 293T cells followed by purification via protein G as described in Nimmerjahn et al., Immunity 23, 41 (2005) and Nimmerjahn and Ravetch, *Science* 310, 1510 (2005). Sialic acid rich antibody variants were isolated from these antibody preparations by lectin affinity chromatography with *Sambucus nigra* agglutinin (SNA) agarose (Vector Laboratories, Burlingame, Calif.). Enrichment for sialic acid content was verified by lectin blotting (see below). Human intravenous immune globulin (IVIG, 5% in 10% maltose, chromatography purified) was purchased from Octapharma (Herndon, Va.). Digestion of human IVIG was performed as described. Kaneko Y. et al., *Exp. Med.* 203, 789 (2006). Briefly, IVIG was digested by 0.5 mg/ml papain for 1 hr at 37° C., and stopped by the addition of 2.5 mg/ml iodoacetamide. Fab and Fc resulting fragments were separated from non-digested IVIG on a HiPrep 26/60 S-200HR column (GE Healthcare, Piscataway, N.J.), followed by purification of Fc and Fab fragments with a Protein G column (GE Healthcare) and a Protein L column (Pierce, Rockford, Ill.). Fragment purity was checked by immunoblotting using anti-human IgG Fab or Fc-specific antibodies. (Jackson ImmunoResearch, West Grove, Pa.). Purity was judged to be greater than 99%. The F4/80 antibody was from Serotec (Oxford, UK). The Ly 17.2 antibody was from Caltag (Burlingame, Calif.). Sheep anti-glomerular basement membrane (GBM) antiserum (nephrotoxic serum, NTS) was a gift from M. P. Madaio (University of Pennsylvania, Philadelphia, Pa.). Soluble Fc receptors containing a C-terminal hexa-hisitidine tag were generated by transient transfection of 293T cells and purified from cell culture supernatants with Ni-NTA agarose as suggested by the manufacturer (Qiagen).

Figure 4:
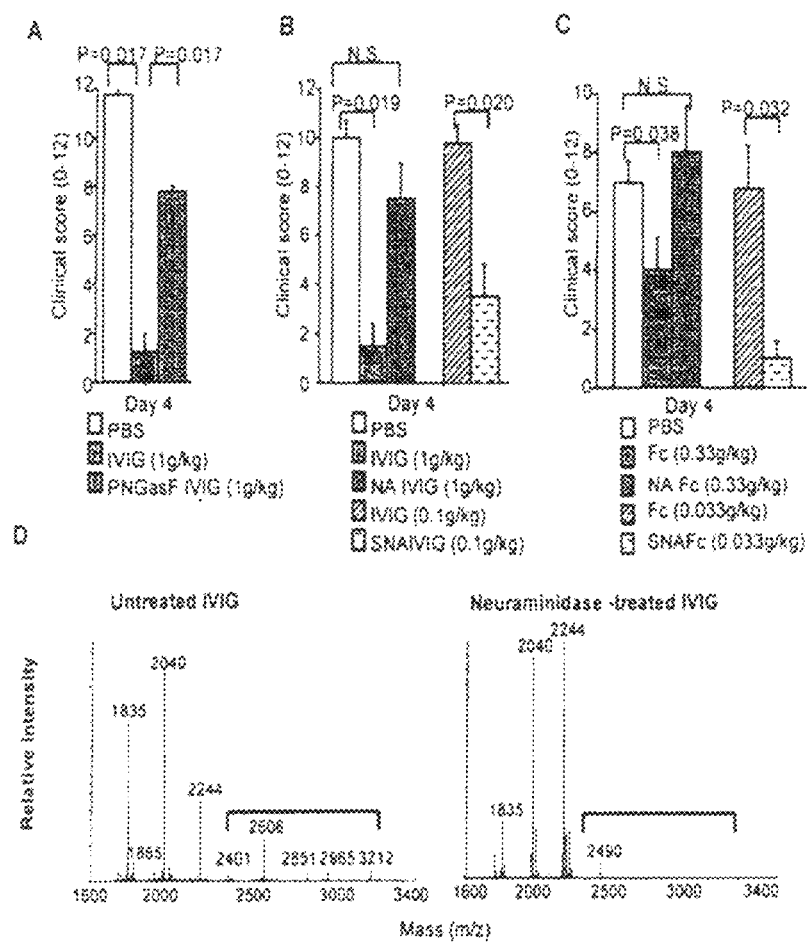
FIG. 4 demonstrates that anti-inflammatory activity of IVIG requires sialic acid. (A) Clinical scores of K/BxN serum-induced arthritis in mice treated with PBS, IVIG, and PNGaseF-treated IVIG (PNGaseF IVIG). (B) In addition to treatment as shown in FIG. 4(A), mice were treated with neuraminidase-treated IVIG (NA IVIG) or SNA-enriched IVIG (SNA IVIG). (C) Clinical scores of mice treated with Fc fragment of IVIG, neuraminidase-treated Fc (NA Fc), or SNA-enriched Fc (SNA Fc) (N=4, mean+/−SEM). (D) Carbohydrate profiles of IVIG preparations. MALDI-TOF-MS profiles of N-glycans derived from untreated or neuraminidase-treated IVIG are shown. Peaks that contain sialic acid residues are indicated by a bracket and the carbohydrate composition of the peaks are presented in FIG. 5. (E) Representative hematoxylin/eosin staining of ankle joints of control mice or K/N induced arthritis mice treated with or without SNA-enriched IVIG (0.1 g/kg). The extensive neutrophil infiltration observed in K/N treated mice is absent from IVIG-SNA (0.1 g/kg) treated mice. (F) Lectin blotting of control Fc fragment of IVIG, neuraminidase-treated Fc (NA Fc) and Fc with high sialic acid content via *Sambucus nigra* agglutinin (SNA) affinity chromatography (SNA Fc). (G) Analysis of 2,3 and 2,6 linked sialic acid residues in IVIG. IVIG was either left untreated (lane2) or treated with a neuraminidase specific for 2,3 linked sialic acid residues (lane3) or a neuraminidase specific for 2,3 and 2,6 linked sialic acid residues (lane 4). Removal of sialic acid was assayed by lectin blotting with SNA (which recognizes 2,6 linked sialic acid residues) and MAL-I (which recognizes 2,3 linked sialic acid residues). As a control for a glycoprotein rich in 2,3 linked sialic acid residues fetuin was used (lane 1). The coomassie stained gel served as a loading control (Coomassie). (H) Anti-inflammatory activity of IVIG depleted in 2, 3 or 2,3 and 2,6 linked sialic acid residues. Mice were injected with KRN serum to induce arthritis and either left untreated (KRN), treated with IVIG (KRN+IVIG), IVIG-depleted in 2,3 linked sialic acid residues (α2-3 sialidase tx IVIG+KRN), or IVIG depleted in 2,3 and 2,6 linked sialic acid residues (α2-3,6 sialidase tx IVIG+KRN). As a negative control mice were injected with PBS (untreated).
Figure 4:
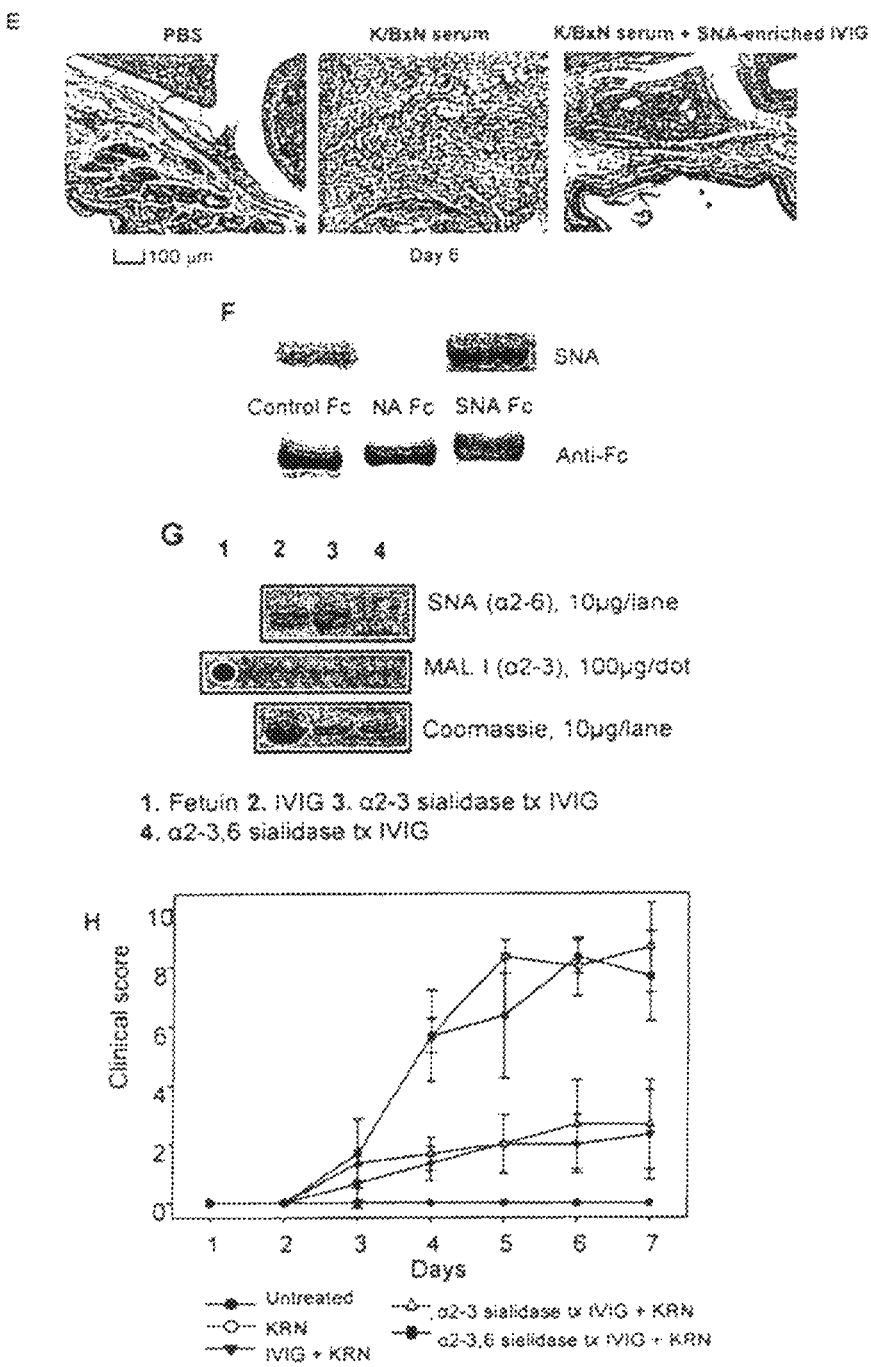
Figure 6:
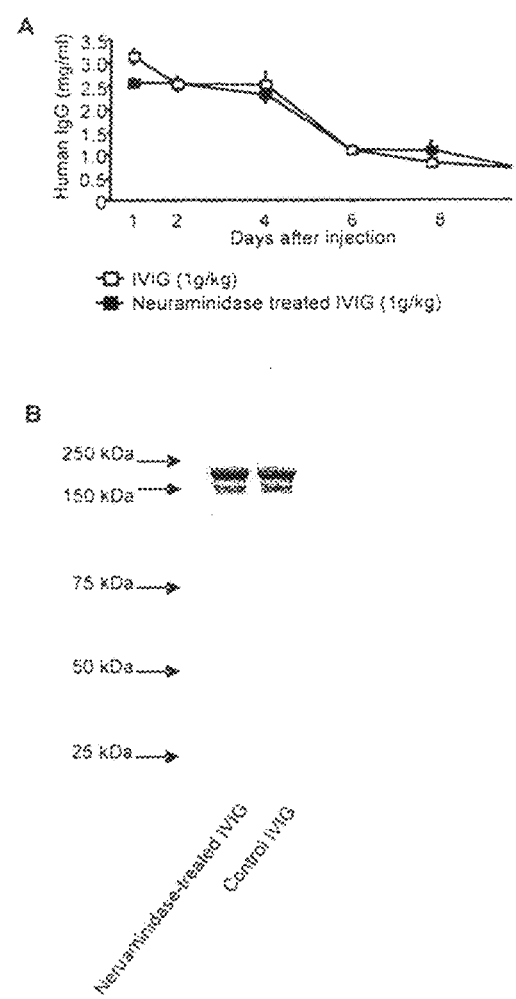
FIG. 6 illustrates serum half-life and protein integrity of de-sialylated IVIG. (A) The level of human IgG in the serum of IVIG treated mice on the indicated days was measured by ELISA (N=4, mean+/−SEM). There was no significant difference in half-life of IVIG and de-sialylated IVIG. Significance was determined by the repeated measure ANOVA-test. (B) Ten microgram of IVIG or de-sialylated IVIG were resolved by SDS-PAGE using an 8% polyacrylamide gel under non-reduced conditions and visualized with coomassie brilliant blue staining. The monomeric composition and structural integrity of IVIG were not affected by neuraminidase treatment.

IVIG was treated with neuraminidase and the composition and structure of the resulting preparation was analyzed by mass spectroscopy. No detectable sialic acid containing glycans remained after neuraminidase treatment (FIGS. 4D, F and 5). These IgG preparations were then tested for their ability to protect mice from joint inflammation induced by passive transfer of K×N serum, an IgG 1 immune complex-mediated inflammatory disease model. De-sialylation with neuraminidase abrogated the protective effect of the IVIG preparation in the K×N serum induced arthritis model (FIG. 4B, C, E). This loss of activity was not the result of reduced serum half-life of the asialylated IgG (FIG. 6A) preparations or the result of changes to the monomeric composition or structural integrity of the IgG (FIG. 6B). Removal of all glycans with PNGase had a similar effect and abrogated the protective effect of IVIG in vivo (FIG. 4A). Selective removal of 2,6 sialic acid linkages abrogated IVIG activity, while removal of 2,3 linkages had no apparent effect (FIG. 4G, H).

Example 3

IVIG Fraction with Enriched Sialic Acid Content Decreases Inflammation in Mouse Arthritis Model Preparation of IVIG with an Increased Content of Sialic Acid Since sialic acid appeared to be required for the anti-inflammatory activity of IVIG, the basis for the high dose requirement (1 g/kg) for this anti-inflammatory activity could be the limiting concentration of sialylated IgG in the total IVIG preparation. The IVIG was fractionated on an SNA-lectin affinity column to obtain IgG molecules enriched for sialic acid modified glycan structures.

Figure 7:
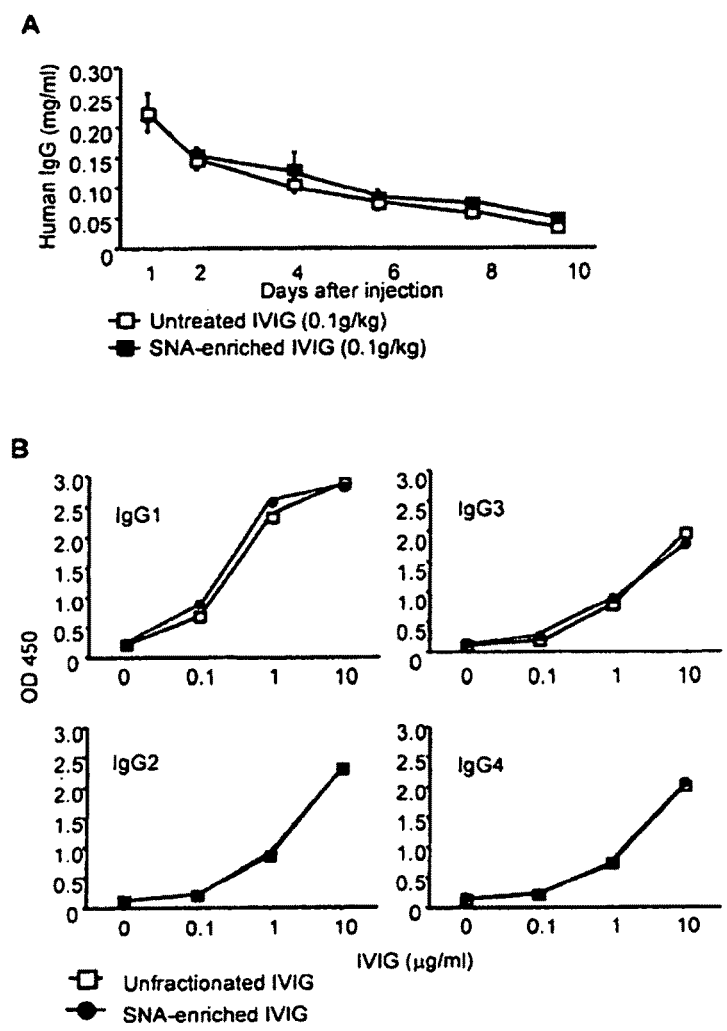
FIG. 7 demonstrates serum half-life and subclass composition of SNA-enriched IVIG. (A) The level of human IgG in the serum of IVIG treated mice at the indicated days was measured by ELISA (N=4, mean+/−SEM). There was no significant difference in half-life of IVIG and the SNA-enriched IVIG fraction. Significance was determined by the repeated measure ANOVA test. (B) IgG subclasses in untreated and SNA-enriched IVIG were determined by ELISA. No differences were observed.
Figure 8:
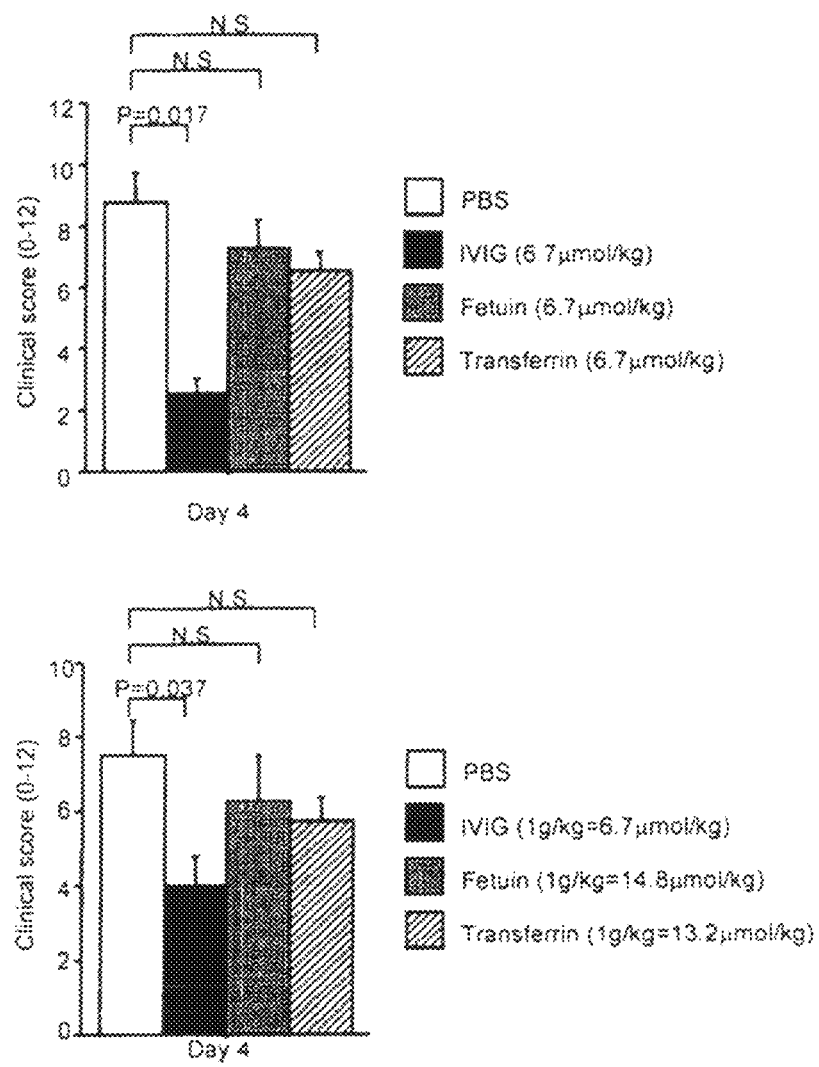
FIG. 8 illustrates that sialylated proteins with similar carbohydrate structures do not protect mice from K/BxN serum induced arthritis. Equivalent molar amounts (6.7 μmol per kilogram) or equal weight (1 g per kilogram) of IVIG or sialo-proteins fetuin and transferrin were administered 1 hr before K/BxN serum injection, and clinical scores were examined on day 4 (N=4, mean+/−SEM). PBS was used as an additional control. Compared to IgG, fetuin or transferrin had no statistically significant anti-inflammatory activity at equivalent molar concentrations. Significance was calculated with the Mann-Whitney's U test.
Figure 9:
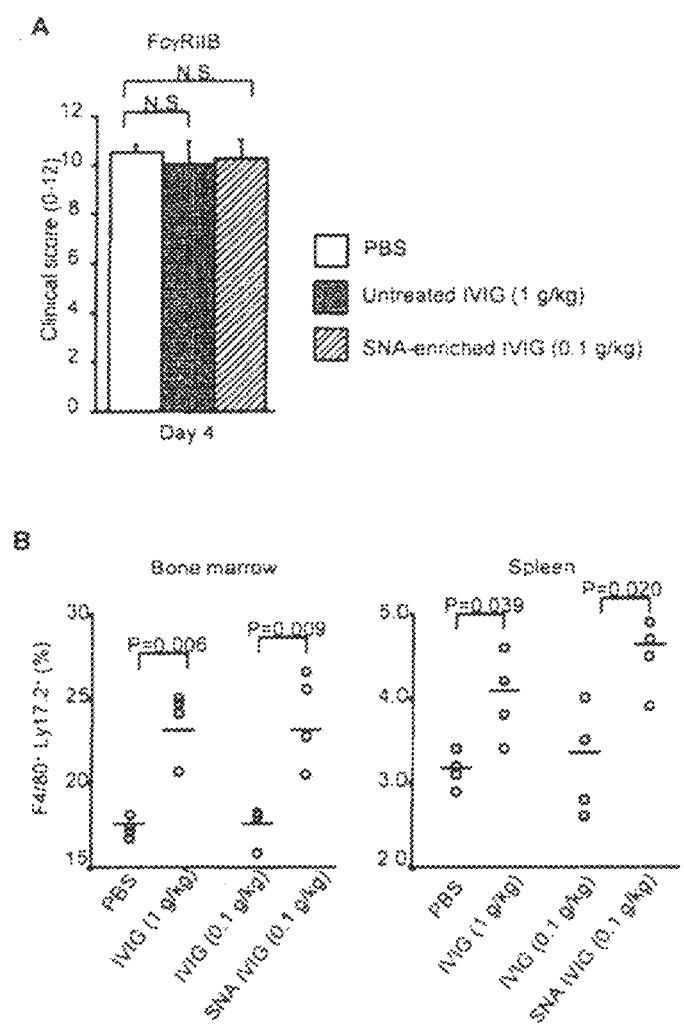
FIG. 9 demonstrates that anti-inflammatory activity of SNA enriched IVIG requires FcγRIIB. (A) Unfractionated IVIG (1 g/kg mouse weight), SNA-enriched IVIG (0.1 g/kg mouse weight), or PBS as a control were injected into FcγRIIB-deficient mice 1 hr before K/BxN serum injection, and clinical scores were examined on day 4 (N=4, mean+/−SEM). There were no significant differences in clinical scores of arthritis. Significance was calculated with the Mann-Whitney's U test. (B) In vivo accumulation of FcγRIIB+ monocytes by SNA-enriched IVIG. Wild type mice were injected with 1 g/kg, 0.1 g/kg IVIG or 0.1 g/kg of SNA-enriched IVIG, or PBS as a control. Bone marrow (left panel) and spleen cells (right panel) were collected and analyzed by flow cytometry 1 day after the injection (N=4). F4/80+FcγRIIB+ cells accumulated significantly after treatment with 1 g/kg of IVIG or 0.1 g/kg of SNA-enriched IVIG. Significance was calculated with the Student's t test.

These sialic acid enriched fractions were tested for protective effects in the K×N serum transfer arthritis model as compared to unfractionated IVIG. A 10 fold enhancement in protection was observed for the SNA-binding fraction, such that equivalent protection was obtained at 0.1 g/kg of SNA-enriched IVIG as compared to 1 g/kg of unfractionated IVIG (FIG. 4B, C). The serum half-life and IgG subclass distribution of the SNA enriched fraction was equivalent to that of unfractionated IVIG (FIG. 7A,B). The effect of sialylation was specific to IgG; sialylated N-linked glycoproteins such as fetuin or transferrin with similar bi-antennary, complex carbohydrate structures had no statistically significant anti-inflammatory activity at equivalent molar concentrations of IgG (FIG. 8). Finally, the mechanism of protection of the sialylated IVIG preparation was similar to unfractionated IVIG in that it was dependent on FcγRIIB expression and resulted in the increased expression of this inhibitory receptor on effector macrophages (FIG. 9).

Example 4

The Increased Anti-Inflammatory Response of IVIG with Increased Sialic Acid Content is Mediated by Sialylation of the N-Linked Glycan on the Fc Domain Since the polyclonal IgG in IVIG may also contain O and N linked glycans on the light chains or heavy chain variable domains that can be sialylated, we confirmed that the increase in anti-inflammatory activity of the SNA-enriched IgG preparation resulted from increased sialylation of the N-linked glycosylation site on the Fc. Fc fragments were generated from unfractionated and SNA fractionated IVIG and tested for their in vivo activity. As observed for intact IgG, SNA-purified Fc fragments were enhanced for their protective effect in vivo when compared to Fc fragments generated from unfractionated IVIG (FIG. 4C). In contrast, Fab fragments displayed no anti-inflammatory activity in this in vivo assay. Thus, the high dose requirement for the anti-inflammatory activity of IVIG can be attributed to the minor contributions of sialylated IgG present in the total preparation. Enrichment of these fractions by sialic acid binding lectin chromatography consequently increased the anti-inflammatory activity.

These results using passive immunization of IgG antibodies indicated that the ability of IgG to switch from a pro-inflammatory to an anti-inflammatory species is influenced by the degree of sialylation of the N-linked glycan on the Fc domain.

Example 5

Increase of Anti-Inflammatory Activity, Mediated by Sialylation of IgG, Occurs During an Active Immune Response Murine Model for Goodpasture's Disease In this model, mice are first sensitized with sheep IgG together with adjuvant and four days later injected with a sheep anti-mouse glomerular basement membrane preparation (nephrotoxic serum, NTS). Briefly, mice were pre-immunized intraperitoneally with 200 μg of sheep IgG (Serotec) in CFA, followed by intravenous injection of 2.5 μl of NTS serum per gram of body weight four days later. Blood was collected from non-treated control mice four days after the anti-GBM anti-serum injection, and serum IgG was purified by Protein G (GE Healthcare, Princeton, N.J.) and sepharose-bound sheep IgG column, generated by covalently coupling sheep IgG on NHS-activated sepharose column (GE Healthcare, Princeton, N.J.), affinity chromatography.

Pre-sensitization followed by treatment with NTS induces mouse IgG2b anti-sheep IgG antibodies (NTN immunized). Kaneko Y. et al., *Exp. Med.*, 203:789 (2006). Mouse IgG2b antibodies are deposited in the glomerulus together with the NTS antibodies and result in an acute and fulminant inflammatory response by the IgG2b mediated activation of FcγRIV on infiltrating macrophages. In the absence of pre-sensitization inflammation is not observed, indicating that the mouse IgG2b anti-sheep IgG antibodies are the mediators of the inflammatory response.

Figure 10:
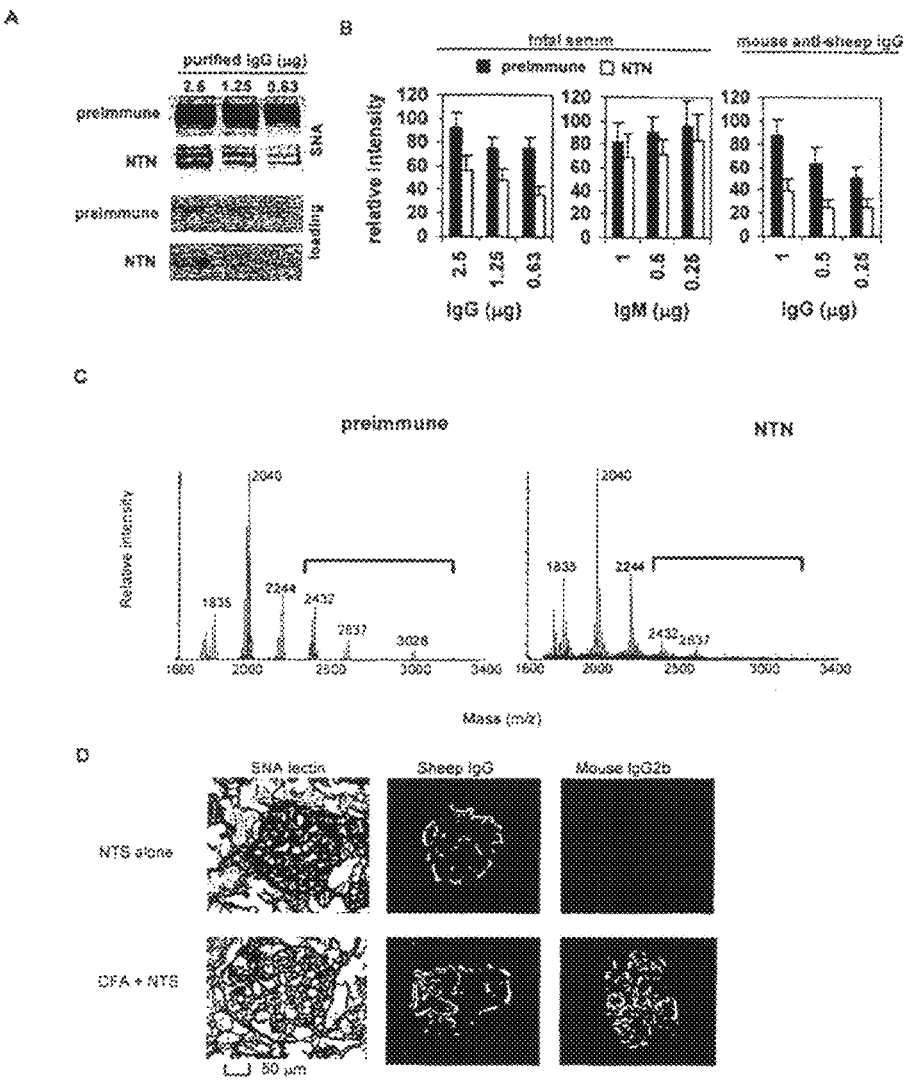
FIG. 10 demonstrates that active immunization results in reduced IgG sialylation. (A) Serum IgG from untreated (preimmune) or mice with nephrotixic nephritis (NTN) induced by immunization with sheep IgG and nephrotoxic serum (NTS) was characterized for sialic acid content by blotting with *Sambucus nigra* agglutinin (SNA) (see methods). (B) Quantitation of the level of sialylation of total serum IgG and IgM antibodies and sheep IgG-specific IgG antibodies in untreated and NTN mice (mean+/−SEM) as determined by densitometry. No detectable sheep IgG was present in the mouse antibody preparations (data not shown). (C) MALDI-TOF analysis of sugar residues attached to IgG antibodies from untreated or NTN mice. Sialic acid containing moieties are indicated by a bracket. The detailed carbohydrate composition of the individual peaks is shown in FIG. 5. (D) Detection of sialic acid content in antibodies deposited in the glomeruli of mice injected with nephrotoxic serum with (NTS+CFA) or without (NTS alone) preimmunization with sheep IgG in complete Freund's adjuvant (CFA).

To determine if active immunization resulting in pro-inflammatory IgG is associated with a change in sialylation, serum IgG and IgM from preimmune and NTS immunized mice were characterized for sialic acid content by SNA lectin binding FIG. 10A,B,C). Total IgG sialylation was reduced on average by 40% in immunized mice as compared to the unimmunized controls. The effect was specific for IgG; sialylation of IgM was equivalent pre and post immunization. This difference in sialylation was more pronounced when the sheep specific IgG fraction from mouse serum was analyzed, showing a 50-60% reduction in sialylation compared to preimmune IgG (FIG. 10B).

These results were confirmed by MALDI-TOF-MS analysis. Monosaccharide composition analysis was performed by UCSD Glycotechnology Core Resource (San Diego, Calif.). Glycoprotein samples were denatured with SDS and 2-mercaptoethanol, and digested with PNGase F. The released mixed N-glycans were purified by reversed-phase HPLC and solid-phase extraction, and then exposed hydroxyl groups of the N-glycans were methylated. The resulting derivatized saccharides were purified again by reversed-phase HPLC and subject to MALDI-TOF-MS.

The analysis of the pre and post immunization IgGs confirmed that the changes in the N-glycan structure were specific to the terminal sialic acids moieties (FIG. 10C). The mouse IgG2b anti-sheep antibodies that were deposited in the glomeruli, previously shown to be responsible for engagement of the FcγRIV bearing, infiltrating macrophages displayed reduced sialic acid content as compared to the pre-immunized controls (FIG. 10D).

All patent and non-patent publications cited in this disclosure are incorporated herein in to the extent as if each of those patent and non-patent publications was incorporated herein by reference in its entirety. Further, even though the invention herein has been described with reference to particular examples and embodiments, it is to be understood that these examples and embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A modified IVIG composition prepared from an unmodified IVIG composition, wherein the modified IVIG composition has (i) increased anti-inflammatory activity as compared to the unmodified IVIG composition, and (ii) a higher content of α2,6 linked sialic acid in the N-linked glycans of Fc regions than the unmodified IVIG composition.

2. The modified IVIG composition of claim 1 wherein the modified IVIG composition has a higher a higher content of α2,6 linked N-acetylneuraminic acid in the N-linked glycans of Fc regions than the unmodified IVIG composition.

3. A pharmaceutical composition comprising the modified IVIG composition of claim 1 and a pharmaceutically acceptable carrier.

4. A pharmaceutical composition comprising the modified IVIG composition of claim 2 and a pharmaceutically acceptable carrier.

\* \* \* \* \*